US006987011B1

(12) United States Patent
Reid et al.

(10) Patent No.: US 6,987,011 B1
(45) Date of Patent: Jan. 17, 2006

(54) PROCESS FOR PRODUCTION OF BIOPOLYMERS FROM NITROGEN DEFICIENT WASTEWATER

(75) Inventors: Nicola Maree Reid, Rotorua (NZ); Alison Hyde Slade, Rotorua (NZ); Trevor Raymond Stuthridge, Rotorua (NZ)

(73) Assignee: New Zealand Forest Research Institute Limited, (NZ)

( * ) Notice: Subject to any disclaimer, the term of this patent is extended or adjusted under 35 U.S.C. 154(b) by 123 days.

(21) Appl. No.: 10/130,682

(22) PCT Filed: Nov. 20, 2000

(86) PCT No.: PCT/NZ00/00234

§ 371 (c)(1),
(2), (4) Date: May 17, 2002

(87) PCT Pub. No.: WO01/36652

PCT Pub. Date: May 25, 2001

(30) Foreign Application Priority Data

Nov. 18, 1999 (NZ) .................................. 501152

(51) Int. Cl.
*C12P 7/62* (2006.01)
(52) U.S. Cl. ..................... 435/135; 435/142; 435/146
(58) Field of Classification Search ................ 435/135, 435/142, 146
See application file for complete search history.

(56) References Cited

U.S. PATENT DOCUMENTS

| 2,897,148 A | | 7/1959 | Laboureur et al. ............. 210/11 |
|---|---|---|---|
| 3,721,622 A | | 3/1973 | Finn et al. ..................... 210/11 |
| 5,990,271 A | * | 11/1999 | Noda .......................... 528/361 |
| 6,022,729 A | * | 2/2000 | Steinbuchel et al. ...... 435/252.3 |
| 6,174,990 B1 | * | 1/2001 | Noda .......................... 528/361 |
| 6,479,145 B1 | * | 11/2002 | Srienc et al. ................ 428/403 |
| 6,610,764 B1 | * | 8/2003 | Martin et al. ................ 523/124 |
| 6,623,641 B1 | * | 9/2003 | Gapes et al. ................ 210/614 |
| 2002/0031812 A1 | * | 3/2002 | Lapointe et al. ............ 435/135 |

FOREIGN PATENT DOCUMENTS

| CA | 1110188 | 10/1981 |
|---|---|---|
| EP | 0 406 032 | 1/1991 |
| EP | 0 970 922 A2 | 1/2000 |
| JP | 3 143397 | 6/1991 |
| JP | 3-169395 | 7/1991 |
| JP | 5-96296 | 4/1993 |
| JP | 5-123694 | 5/1993 |
| JP | 10-005789 | 1/1998 |
| WO | WO 89/06274 | 7/1989 |
| WO | WO 99-62833 | 12/1999 |
| WO | WO 00/52189 | 9/2000 |

OTHER PUBLICATIONS

Durner et al Accumulation of Poly(R)-3-Hydroxyalkanoates in Pseudomonas oleovorans Applied and Environmental Microbiology, Aug. 2000, p. 3408-3414, vol. 66, No. 8.*
Chua, Hong, et al. "Accumulation of Biopolymers in Activated Sludge Biomass." *Applied Biochemistry and Biotechnology*, vol. 77-79 (1999) pp. 389-399.
Yu, Peter H., et al. "Conversion of Food Industrial Wastes into Bioplastics with Municipal Activated Sludge." *Macromolecular Symposia*. vol. 148 (1999) pp. 415-424.
Braunegg, Gerhart, et al. "Polyhydroxyalkanoates, biopolyesters from renewable resources: Physiological and engineering aspects." *Journal of Biotechnology*. vol. 65 (1998) pp. 127-161.
de Koning, Gertjan, et al. "A Process for the Production of Bacterial Medium-Chain-Length Poly [(R)-3-Hydroxyalkanoates]: Reviewing the Status Quo." *1996 International Symposium on Bacterial Polyhydroxyalkanoates*. (1997) pp. 137-142.
Pal, S., et al. "Nutritional and Cultural Condition for Production of Poly-3-hydroxybutyric Acid by *Azobacter chroococcum*." *Folia Microbiologica*. vol. 43(2) (1998) pp. 177-181.
Holowach, L.P., et al. "Bacterial Conversion of a Waste Stream Containing Methyl-2-hydroxyisobutyric Acid to Biodegradeable Polyhydroxyalkanoate Polymers." *American Chemical Society Symposium Series*. vol. 575 (1994) pp. 202-211.
Asenjo, Juan A. And Julie S. Suk. "Kinetics and Models for the Bioconversion of Methane into an Intracellular Polymer, Poly-βHydroxybutyrate (PBH)." *Biotechnology and Bioengineering Symposium No. 15*. (1985) pp. 225-234.
Kellerhals, Michele B, et al. "Development of a closed-loop control system for production of medium-chain-poly(3-hydroyalkanoates) (mcl-PHAs) from bacteria." *Macromolecular Symposia*. vol. 114. (1999) pp 358-389.
Stante, L., et al. "Production of Poly-β-Hydroxybutirate by Lampropedia Spp. Isolated from Activated Sludge for Phosphorus Removal." *Mededelingen— Faculteit Landouwkundige en Toegepast*. No. 61/4b (1996) pp. 2101-2108.

(Continued)

*Primary Examiner*—Herbert J. Lilling
(74) *Attorney, Agent, or Firm*—Factor & Lake

(57) ABSTRACT

A process for producing biopolymers comprises passing nitrogen deficient wastewater through a treatment system comprising micro-organisms which grow aerobically in nitrogen deficient wastewater, and controlling the environment in the treatment system by maintaining a sufficiently stable dissolved oxygen level to thereby encourage the growth and/or activity of micro-organisms which produce the biopolymers, and recovering the biomass produced and the biopolymers.

27 Claims, 3 Drawing Sheets

OTHER PUBLICATIONS

Comeau, Yves, et al. "Determination of Poly-β-Hydroxybutyrate and Poly-βHydroxyvalerate in Activated Sludge by Gas-Liquid Chromatography." *Applied and Environmental Microbiology.* vol. 54 No. 9 (1988) pp. 2325-237.

Beccari, M., et al. "A Bulking Sludge with High Storage Response Selected Under Intermittent Feeding." *Water Research.* vol. 12 No. 11 (1998) pp. 3403-3413.

Liu, Fang, et al. "Production of Poly-β-hydroxybutyrate on Molasses by Recombinant *Escherichia coli.*"0 *Biotechnology Letters.* vol. 20 No. 4 (1998) pp. 345-34.

Page, William J., et al. "Formation of Poly (Hydroxybutyrate-Co-Hydroxyvalerate) by *Azotobacter vinelandii* UWD." *Applied and Environmental Microbiology.* vol. 58 No. 9 (1998) pp. 2886-2873.

Son, Hongjoo, et al. "Growth-Associated Production of Poly-β-hydroxybutyrate from Glucose or Alcoholic Distillery Wastewater by *Actinobacillus* Sp. EL-9." *Biotechnology Letters.* vol. 18 (1996) pp. 1229-1234.

Takeda, M., et al. "Biosynthesis of Poly(3-hydroxybutyrate-Co-3-hydroxyvalerate) by a Mutant of *Sphaerotilus natans* ." *Applied Microbiology and Biotechnology.* vol. 44 (1995) pp. 37-42.

Ahn, Woo Suk, et al. "Production of Poly(3-Hydroxybutyrate) by Fed-Batch Culture of Recombinant *Escherichia coli* with a Highly Concentrated Whey Solution." *Applied and Environmental Microbiology.* vol. 66 No. 8 (2000) pp. 3624-3627.

Wallen, Lowell L. and William K. Rohwedder. "Poly-β-hydroxyalkanoate from Activated Sludge." *Environmental Science and Technology.* vol. 8. (1974) pp. 576-579.

Hu, W.F., et al. "Synthesis of Poly(3-hydroxybutyrate-co-3-hydroxyvalerate) from Activated Sludge." *Biotechnology Letters.* vol. 19 No. 7 (1997) pp. 695-698.

Satoh, H., et al. "Activated Sludge as a Possible source of Biodegradable Plastic." *Water Science and Technology.* vol. 38 No. 2 (1998) pp. 103-109.

Shimizu, Hiroshi, et al. "Maximum Production Strategy for Biodegradable Copolymer P(HB-co-HV) in Fed-Batch Culture of Alcaligenes europhus." *Biotechnology and Bioengineering.* vol. 62 No. 5 (1999) pp. 518-525.

Wang, Fulai and Sang Up Lee. "Poly(3-Hydroxybutyrate) Production with High Productivity and High Polymer Content by a Fed-Batch Culture of Alcaligenes latus under Nitrogen Limitation." *Applied and Environmental Microbiology.* vol. 63 No. 9 (1997) pp. 3703-3706.

van Loosdrecht, M. C. M., et al., "Importance of Bacterial Storage Polymers in Bioprocesses." *Water Science and Technology.* vol. 33 No. 1 (1997) pp. 41-47.

Senior, P.J. and E.A. Dawes. "Poly-β-Hydroxybutyrate Biosynthesis and the Regulation of Glucose Metabolism in Azobacter beijerinckii." *Biochemical Journal.* vol. 125 (1971) pp. 55-66.

Chua, H., et al. "Coupling of Waste Water Treatment with Storage Polymer Production." *Applied Biochemistry and Biotechnology.* vol. 63-65 (1997) pp. 627-635.

Page, William J. and Olga Knospi. "Hyperproduction of Poly-β-Hdyroxybutyrate during Exponential Growth of Azotobacter vinelandii UWD." *Applied and Environmental Microbiology.* vol. 55 No. 6 (1989) pp. 1334-1339.

Lee, Eun Yeol, et al. "Biosynthesis of Poly(3-Hydroxybutyrate-co-3-Hydroxyvalerate) by Newly Isolated *Agrobacterium* sp. SH-1 and GW-014 from Structurally Unrelated Single Carbon Substrates." *Journal of Fermentaion and Bioengineering.* vol. 79 (1995) pp. 328-334.

Page, William J. "Production of poly-β-hdyroxybutyrate by *Azotobacter vinelandii* strain UWD during growth on molasses and other complex carbon sources." *Applied Microbiology and Biotechnology.* vol. 31 (1989) pp. 329-333.

Hassan, Mohd Ali, et al. "Acetic Acid Separation from Anaerobically Treated Palm Oil Mill Effluent by Ion Exchange Resins for the Production of Polyhydroxyalkanoate by Alacaligenes eutrophus." *Bioscience, Biotechnology, Biochemistry.* vol. 61 No. 9 (1997) pp. 1465-1468.

Madison, Laura and Gjalt W. Huisman. "Metabolic Engineering of Poly(3Hdyroxyalkanoates): From DNA to Plastic." *Microbiology and Molecular Biology Reviews.* vol. 63 (1999) pp. 21-53.

Bruce, Mary E. and Thomas A. Clark, "Klebsiella and nitrogen fixation in pulp and paper mill effluents and treatment systems," *Appota.* vol. 27 (1993) pp. 231-237.

Clark, Thomas A., et al. "Nitrogen fixation in an aerated stabilization basin treating bleached kraft mill wastewater." *Environment Research.* vol. 69 No. 5 (1997) pp. 1039-1046.

Gapes, D.J., et al. "Nitrogen Fixation in the Treatment of Pulp and Paper Wastewaters." *Water Science and Technology.* vol. 49 (1999) pp. 85-92.

* cited by examiner

PROCESS FOR PRODUCTION OF BIOPOLYMERS FROM NITROGEN DEFICIENT WASTEWATER

FIELD OF INVENTION

The invention comprises a process for the production of biopolymers from nitrogen-deficient wastewater, such as wastewater from pulp and paper production.

BACKGROUND

Aerobic biological processes are commonly used in the treatment of industrial wastewater, before discharge to the environment. In such processes micro-organisms consume wastewater contaminants, and are encouraged to proliferate in reactor systems under intensive aeration. A variety of process configurations are known, such as activated sludge, moving bed biofilm reactors, membrane bioreactors, aerated lagoons and aerated stabilisation basins. Aerated lagoons and aeration stabilisation basins are examples of low rate biological treatment systems, whilst activated sludge and variant systems and moving bed biofilm reactors are high rate biological treatment systems.

Pulp and paper mill wastewaters are typically deficient in nutrient nitrogen required to support bacterial growth for biological treatment. Conventionally activated sludge processes used in the pulp and paper industry are operated with the addition of nitrogen to the system, typically in the form of urea. Other industrial wastewaters can also be nitrogen-deficient. By "nitrogen-deficient wastewater" is meant wastewater for which, due to lack of available nitrogen in the wastewater, an additional nitrogen source is required for the biological consumption of the biodegradable organic material present.

It has also previously been proposed to use industrial wastewaters to produce biopolymers having economic value. For example Japanese patent application 3143397 discloses a method for the production of a polyhydroxyalkanoate (PHA) wherein a carbon source is added to an activated sludge so as to raise microbial numbers. Denitrification of this culture is then required prior to its aerobic culture under nitrogen deficient conditions to achieve the intracellular accumulation of polyhydroxybutyric acid. Japanese patent 2514131 requires wastewater to be treated to undergo an initial anaerobic acid fermentation so as to achieve a conversion of the organic content of the wastewater to carboxylic acids. The fermented wastewater then undergoes a nitrogen removal step prior to its use as a feed for nitrogen fixing micro-organisms. Application of this method for the production of polymers, such as PHAs accumulated in the nitrogen-fixing micro-organisms, is also disclosed. Both methods require removal of nitrogen in a separate step, prior to the use of the wastewater for the production of polymer.

SUMMARY OF INVENTION

The invention provides an improved or at least alternative process for the production of hydroxyalkanoic acids or their polymers from wastewaters.

In broad terms the invention comprises a process for producing biopolymers comprising passing nitrogen deficient wastewater through a treatment system comprising micro-organisms which grow aerobically in nitrogen deficient wastewater and controlling the environment in said treatment system by maintaining a sufficiently stable dissolved oxygen level to thereby encourage the growth and/or activity of micro-organisms which produce the biopolymers, and recovering biomass produced and the biopolymers.

Typically the dissolved oxygen level in the treatment system is monitored and aeration is controlled to maintain a substantially stable dissolved oxygen level. The pH, temperature, loading rate and any nutrient addition will generally be conventional.

Ideally the process is also operated to remove contaminants from the wastewater and the dissolved oxygen is maintained at a level which also optimises organic matter removal in relation to biomass or biopolymer yield.

Preferably the process also includes maintaining a sufficiently stable dissolved oxygen level in the treatment system to also encourage the growth and/or activity of nitrogen-fixing micro-organisms, so that nitrogen supplementation is not required.

Preferably the biopolymer produced comprises a hydroxyalkanoic acid or a polyester thereof. Preferably the polyhydroxyalkanoate polyester produced includes 3-hydroxybutyric acid and/or 3-hydroxyvalerate and/or 3-hydroxyhexanoate and/or other hydroxyalkanoic acid congeners.

Preferably the process includes maintaining the dissolved oxygen level at a stable level selected to thereby select the polymer composition of the biopolymer(s) produced such as the relative proportion of congeners.

Typically the wastewater is pulp and paper wastewater but the process of the invention may alternatively be applied to any other nitrogen-deficient industrial wastewater.

Typically the nitrogen-deficient wastewater may have a biochemical oxygen demand (BOD) to nitrogen (N) ratio of greater than 100:5, more typically greater than 100:2, most typically greater than 100:1.

Typically the treatment system is a high rate biological treatment system such as an activated sludge system.

The micro-organisms may be indigenous to the wastewater and the process conditions are controlled to encourage growth of the required isolates of species, or the wastewater may be seeded with biopolymer producing and/or nitrogen fixing micro-organisms. One or more of the micro-organisms may be immobilised or restricted to a solid support submerged or held within the wastewater being treated.

BRIEF DESCRIPTION OF THE FIGURES

The invention is further described with reference to the accompanying figures which are referred to in the examples in which.

DETAILED DESCRIPTION

Figure 1:
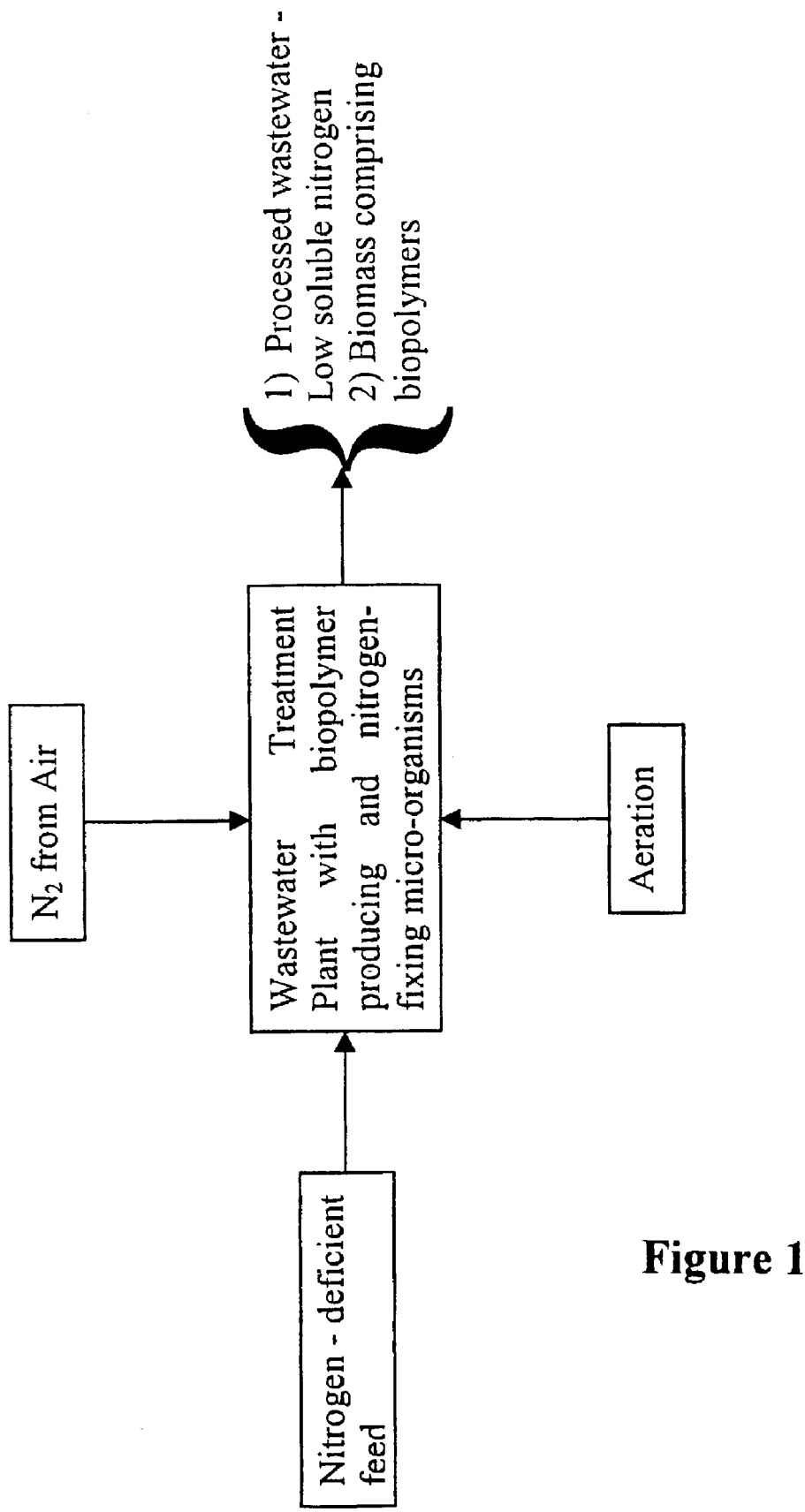
FIG. 1 schematically shows one form of the process of the invention.

We have found that by maintaining a sufficiently stable dissolved oxygen level in an aerobic biological treatment system comprising as a media nitrogen deficient wastewater, the growth and accumulation of PHA or other biopolymer producing micro-organisms occurs and is encouraged. Nitrogen-deficient wastewater is supplied to a treatment system such as an activated sludge system, which is typically operated at a normal operating pH, phosphorus level and temperature to facilitate biological growth, and with monitoring of the dissolved oxygen level and aeration control to maintain the dissolved oxygen level at a substantially stable level. The dissolved oxygen level is controlled at a level which is optimum for production of the biopolymers and preferably also efficient removal of organic matter, whilst producing an acceptable biomass yield. The stability of the dissolved oxygen level is believed to be of greater significance than the specific level.

Some industrial wastewater such as pulp and paper wastewater typically has a low nitrogen content relative to the organic carbon content. Nitrogen may be added as urea or in another form. However in the process of the invention the micro-organisms may also obtain sufficient nitrogen for growth by fixation of atmospheric nitrogen. Maintaining a substantially stable dissolved oxygen level also encourages nitrogen-fixing micro-organisms.

Known processes for producing biopolymers from pulp and paper wastewater may require anaerobic fermentation before aerobic growth of the biopolymer producing micro-organisms. We have found that in the process of the invention micro-organisms from pulp and paper wastewater can produce PHAs without the requirement for an anaerobic fermentation prior to the productive growth of PHA producing micro-organisms.

The process of the invention is effectively carried out in an activated sludge treatment system, but may potentially be applied to other forms of high rate system. With an activated sludge system, the dissolved oxygen level, coupled with organic loading, solids retention time, and food to micro-organism ratio, is selected to give the best production of biopolymers, such as PHAs, and optionally removal of organic matter (as measured by COD, BOD or TOC). An activated sludge system for example may comprise multiple tanks or zones operating under different conditions and in such a multi tank/zone system the process of the invention may operate in, for example, two separate environments each having a different but stable dissolved oxygen level. For example a first tank/zone may optimise organics removal while a second tank/zone may be used to optimise PHA production. Both tanks may be nitrogen-fixing environments. In addition a PHA producing, nitrogen-fixing system of the invention, whether as a single or multi-tank system, may be used in conjunction with and prior to a conventional non-nitrogen-fixing system to process nitrogen-deficient wastewater, without the need for supplementary nitrogen, to produce PHAs and processed wastewater having a low soluble nitrogen content.

We have also found that it is possible to control the polymer composition of PHA polymer produced and in particular the relative proportion of congeners, by selecting the dissolved oxygen level at which the process is run. The polymer composition may comprise hydroxybutyrate, hydroxyvalerate and other higher carbon chain hydroxy-aliphatic acids. Different proportions of congeners are produced by different dissolved oxygen levels. For example, we have found that a greater hydroxy-valerate fraction may be produced at lower dissolved oxygen concentrations and a lower hydroxy-valerate fraction maybe produced at higher dissolved oxygen concentrations.

Under the conditions of the process of the invention PHA producing and optionally also nitrogen-fixing micro-organisms will proliferate. However seeding of the treatment system with appropriate organisms is not excluded. Micro-organisms that contain members known to fix nitrogen and/or produce PHAs which could be used to seed the treatment system include: Azotobacteraceae, Enterobacteraceae, Spirochaetaceae, Rhizobiaceae, Pseudomonadaceae, Rhodospirillaceae, Chromatiaceae, Bacillaceaeae, Methlococcaceae, *Beijerinckia* spp, *Derxia* spp, *Azospirillum* spp, *Xanthobacter* spp, *Azorhizobium* spp.

The above is not intended to be exhaustive and there may be other species of biopolymer producing and/or nitrogen-fixing organisms which may be equally or more effective in the process of the invention.

The invention is further illustrated by the following non-limiting examples:

EXAMPLE 1

Production of intracellular biopolymers and removal of soluble organic material (COD(s)) was studied in a continuous stirred tank reactor (CSTR) system without recycle under three different feed substrate concentrations. The CSTR was operated under nitrogen fixing conditions of controlled dissolved oxygen. The BOD:N ratio was approximately 100:0.3.

Table 1 gives a summary of the main parameters obtained in this work for the three different feed substrate concentrations.

TABLE 1

Biomass N and treatment performance data obtained from CSTR

| Parameter | | Condition 1 | Condition 2 | Condition 3 |
| --- | --- | --- | --- | --- |
| Feed COD(s) | mg/L | 450 | 840 | 630 |
| HRT | d | 0.5 | 0.5 | 0.5 |
| Dissolved oxygen | % | 30 | 30 | 30 |
| Observed yield | mgTSS/mgCOD | 0.18–0.26 | 0.14–0.19 | 0.14–0.19 |
| COD(s) removed | mg/L | 180–252 | 590–630 | 388–426 |
| | % | 44–53 | 72–74 | 63–66 |
| Reactor biomass | mg/L | 47–57 | 107–129 | 70–86 |
| N-fixation rate | mgN/mgTSS.d | 0.09–0.16 | 0.13–0.15 | 0.12–0.15 |
| Biomass N | mgN/mgTSS | 0.04–0.07 | 0.06–0.07 | 0.06–0.07 |
| Biomass P | mgP/mgTSS | .002–007 | .007–.013 | 0.070.011 |

Table 1 presents data on the nitrogen content of the biomass. For all feed substrate concentrations, the nitrogen content of the biomass was low (0.07 mg N/mg TSS or 7%) compared with 12%, the average composition of cell tissue (Pirt, 1975). The low values observed in this system were attributed to the intracellular storage of polymers resulting in an increased C:N ratio due to high cellular carbon content and low biomass nitrogen concentrations. This was confirmed with microscopic examination using a stain specific for the detection of PHAs.

TABLE 2

Description of isolates from a pulp and paper waste treatment system that tested positive for PHA production

|  | Isolate 1 | Isolate 2 | Isolate 3 | Isolate 4 |
|---|---|---|---|---|
| Colony morphology on NFMSA agar | large, brown, irregular, raised, tough | yellow, round smooth, glistening | bright yellow, dry, small, round | creamy-brown, round, smooth |
| Cell morphology (5 day old cultures on NFMS agar) | curved rods | dumbell rods | small dumbell rods | long dumbell rods |
| 16S rDNA sequence identification | *Azorhizobium* spp. | *Xanthobacter* spp. | *Xanthobacter* spp. | *Xanthobacter* spp. |
| PHA stain | + | + | + | + |
| Ability to fix nitrogen | + | + | + | + |

Figure 2:
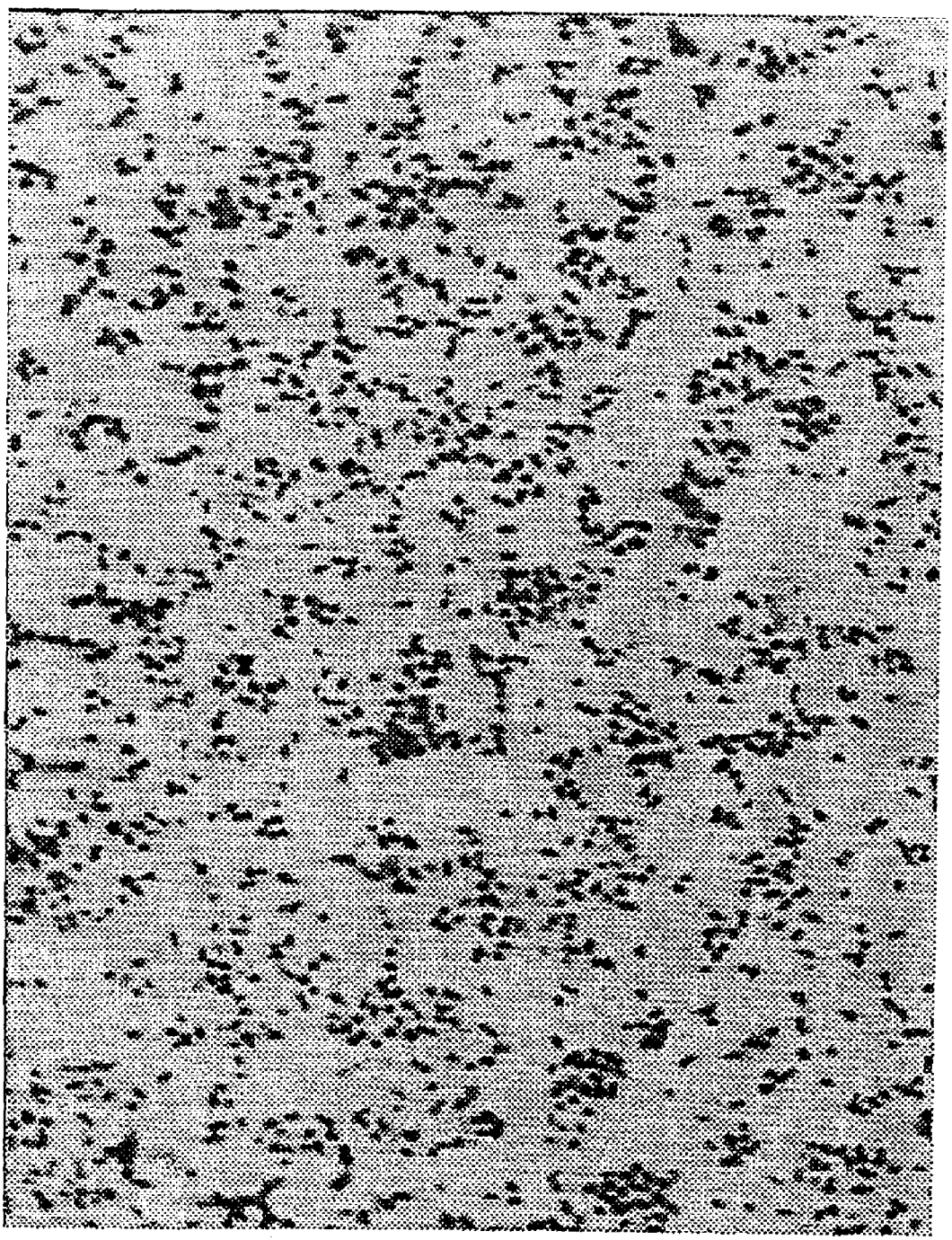
FIG. 2 is a photomicrograph of isolate 8 (PHA stain, 1000× magnification) which is referred to in example 3.

The PHA staining technique of (Gerhardt et al., 1994) was used. Using this technique PHA granules stain darkly against a lighter background, as illustrated in FIG. 2.

The above results evidence that PHA can be synthesised by micro-organisms indigenous to the treatment system with good treatment performance (as measured by COD(s) removal) in a nitrogen-fixing pulp and paper treatment system.

EXAMPLE 2

A nitrogen fixing bioreactor treating a pulp and paper wastewater with a BOD:N ratio of approximately 100:0.8 was operated under nitrogen-fixing conditions. Samples from the mixed liquor were characterised and quantified using a transesterification ethyl/propyl-ester derivatisation and GC-MS technique.

A range of PHA contents between 1.2% to 11% dry weight of biomass were measured in the microbial biomass.

Figure 3:
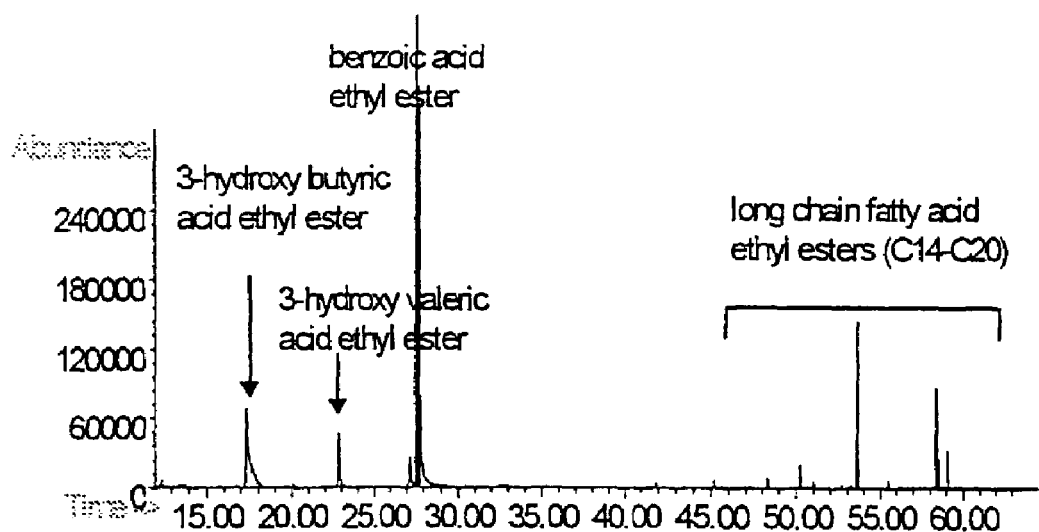
FIG. 3 is a total ion chromatogram of ethyl ester derivatives of an extract from biomass from nitrogen deficient wastewater, produced as described in example 3, confirming production of PHA.

FIG. 3 is a chromatogram showing the abundance of ethyl ester derivatives of an extract from the nitrogen fixing bioreactor. The PHA produced consisted of 3-hydroxybutyrate (3HB), 3-hydroxyvalerate (3HV) and 3-hydroxyhexanoate units. Benzoic acid was used as an internal standard. It has been observed that PHAs with different relative monomer compositions were produced under different bioreactor conditions.

EXAMPLE 3

The following results were obtained from a single stage activated sludge pilot plant. The feed to the pilot plant was thermomechanical pulping wastewater (TMP) with a BOD:N ratio of 100:0.8 and a loading rate of $BOD_5$ 1.07 kg $BOD_5.m^{-3}.d^{-1}$. Nitrogen was not supplemented. Dissolved oxygen was controlled at 14% in phase one of the experiment and 5% during phase two of the experiment.

TABLE 3

PHA production from a nitrogen-fixing activated sludge system treating pulp and paper wastewater

| Nominal DO setting, % | DO level, % mean +/− 95% Cl | Total PHA production*, g/kg dry weight biomass | 3-OH-butyrate, % total PHA* | 3-OH-valerate, % total PHA* | valerate to butyrate ratio |
|---|---|---|---|---|---|
| 14 | 13.79 +/− 0.02 | 41 | 83 | 17 | 0.20 |
|  | 13.75 +/− 0.01 | 30 | 80 | 20 | 0.24 |
|  | 13.76 +/− 0.04 | 68 | 83 | 17 | 0.20 |
|  | 13.54 +/− 0.06 | 25 | 70 | 30 | 0.43 |
|  | mean | 41 | 79 | 21 | 0.27 |
|  | 95% Cl | 19 | 6 | 6 | 0.10 |
| 5 | 4.46 +/− 0.02 | 44 | 47 | 53 | 1.15 |
|  | 4.57 +/− 0.13 | 39 | 48 | 52 | 1.07 |
|  | 4.53 +/− 0.04 | 40 | 70 | 30 | 0.43 |
|  | mean | 41 | 55 | 45 | 0.88 |
|  | 95% Cl | 3 | 15 | 15 | 0.45 |

*hydroxybutyrate and hydroxyvalerate only congeners analysed in this example

Biomass production rates: Pilot sludge discharge: 135.5 liters per cubic meter wastewater per day. Sludge dry weight concentration: 5 g/L wasted sludge.

Sludge discharge rate: 677.5 g per cubic meter wastewater per day. PHA yield: 40 g/kg dry weight sludge.

PHA production rate: 27 g PHA per cubic meter wastewater per day.

The results show that polyhydroxyalkanoates (PHAs) were produced from nitrogen deficient treatment system without nitrogen supplementation or the requirement of a nitrogen removal step. In this example, PHA composition was changed by selecting the dissolved oxygen concentration, with a greater hydroxyvalerate fraction being produced under lower dissolved oxygen concentrations. Hydroxyalkanoate monomeric composition determines the physical properties of the PHA polymer. For example, higher ratios of the $C_5$–$C_{12}$ congeners lead to softer plastics. This example demonstrates that it is possible to alter the ratios of the congeners, such as hydroxybutyric and hydroxyvalerate acids and thereby control the physical properties of the polymer composition.

The foregoing describes the invention and examples thereof. Alterations and modifications as will be obvious to those skilled in the art are intended to be incorporated in the scope hereof.

REFERENCES

Gerhardt, P., Murray, R., Wood, W., Krieg, N., eds. (1994). *Methods for general and molecular bacteriology*. Washington D.C. American Society for Microbiology Pirt, S. J. (1975). *Principles of microbe and cell cultivation*. Oxford, Blackwell Scientific Publications.

The invention claimed is:

1. A process for producing biopolymers comprising hydroxyalkanoic acid or a polyester thereof, the process comprising passing nitrogen deficient wasewater through a treatment system comprising microorganisms which grow aerobically in nitrogen deficient wastewater, and controlling the environment in said treatment system by maintaining a sufficiently stable dissolved oxygen level to thereby encourage the growth of microorganisms which produce the biopolymers, allowing biomass and bipolymer production, and recovering the biomass produced and the biopolymers.

2. A process according to claim 1 wherein the stable dissolved oxygen level also encourages the biopolymer production activity of the microorganisms.

3. A process for producing biopolymers comprising hydroxyalkanoic acid or a polyester thereof, the process comprising passing nitrogen deficient wastewater through a treatment system comprising microorganisms which grow aerobically in nitrogen deficient wastewater, and controlling the environment in said treatment system by maintaining a sufficiently stable dissolved oxygen level to thereby encourage the biopolymer production activity of microorganisms which produce the biopolymers, allowing biomass and biopolymer production, and recovering the biomass produced and the biopolymers.

4. A process according to claim 1 wherein the stable dissolved oxygen level in the treatment system encourages the growth and/or activity of nitrogen-fixing microorganisms.

5. A process according to claim 1 wherein the polyhydroxyalkanoate polyester produced includes 3-hydroxybutyric acid and/or 3-hydroxyvalerate and/or 3-hydroxyhexanoate and/or other hydroxyalkanoic acid congeners.

6. A process according to claim 1 wherein the process excludes a transition from anaerobic to aerobic culture conditions or a requirement for a nitrogen supplementation or nitrogen removal step.

7. A process according to claim 1 wherein the BOD: nitrogen ratio in the nitrogen-deficient wastewater is greater than 100:5.

8. A process according to claim 1 wherein the BOD: nitrogen ratio in the nitrogen-deficient wastewater is greater than 100:2.

9. A process according to claim 1 wherein the BOD: nitrogen ratio in the nitrogen-deficient wastewater is greater than 100:1.

10. A process according to claim 1 wherein the wastewater is nitrogen deficient wastewater resulting from pulp or pulp and paper production.

11. A process according to claim 1 where operational conditions within the treatment system are selected and maintained to achieve good treatment performance and biopolymer production in a recoverable form.

12. A process according to claim 1 where operational conditions within the treatment system are selected and maintained to determine biopolymer composition.

13. A process according to claim 1 including controlling aeration in the treatment system to maintain said substantially stable dissolved oxygen level.

14. A process according to claim 1 including maintaining the dissolved oxygen level at a stable level selected to also achieve good treatment performance in relation to organic matter removal.

15. A process according to claim 1 including maintaining the dissolved oxygen level at a stable level selected to thereby select a polymer composition of the biopolymer(s) produced.

16. A process according to claim 15 including maintaining the dissolved oxygen level at a stable level selected to thereby select the relative proportions of congeners of a polyhydroxyalkanoate polymer produced.

17. A process according to claim 16 including selecting between a lower dissolved oxygen concentration to increase the relative proportion of congeners and a higher dissolved oxygen concentration to decrease the relative proportion of congeners produced.

18. A process according to claim 1 wherein the dissolved oxygen level is maintained stable at a selected level between 5 and 30%.

19. A process as claimed in claim 18 wherein the oxygen level selected is 5%, 14% or 30%.

20. A process according to claim 1 wherein the treatment system is a high rate biological treatment system.

21. A process according to claim 20 wherein the high rate biological treatment system is an activated sludge system.

22. A process according to claim 1 wherein the treatment system includes one controlled zone in which the dissolved oxygen level is maintained at a level which optimizes biopolymer production and another controlled zone in which the dissolved oxygen level is maintained at a level which optimizes treatment performance in relation to organic matter removal.

23. A process according to claim 1 further including subsequently treating an outflow from the controlled environment through a conventional wastewater treatment plant including non-nitrogen-fixing organisms, without nitrogen supplementation.

24. A process according to claim 1, which is carried out with nitrogen supplementation.

25. A process according to claim 1 wherein the controlled environment is seeded with biopolymer-producing and/or nitrogen-fixing micro-organisms.

26. A process according to claim 1 wherein the process is a continuous process.

27. A process according to claim 3 wherein the polyhydroxyalkanoate polyester produced includes 3-hydroxybutyric acid and/or 3-hydroxyvalerate and/or 3-hydroxyhexanoate and/or other hydroxyalkanoic acid congeners.

* * * * *